United States Patent [19]

Iwasaki et al.

[11] 4,123,254
[45] Oct. 31, 1978

[54] GERMICIDAL HERBICIDE FOR AGRICULTURE AND HORTICULTURE

[75] Inventors: Tetsuji Iwasaki; Norioki Miyamoto; Yukio Sugimura; Kyozaburo Tachibana; Tsuneyuki Takeno, all of Wakayama, Japan

[73] Assignee: Kao Soap Co., Ltd., Tokyo, Japan

[21] Appl. No.: 809,023

[22] Filed: Jun. 22, 1977

[30] Foreign Application Priority Data

Jun. 30, 1976 [JP] Japan .................. 51/77194
Jun. 30, 1976 [JP] Japan .................. 51/77197

[51] Int. Cl.$^2$ .................. A01N 9/12; A01N 9/14
[52] U.S. Cl. .................. 71/98; 71/103; 424/314
[58] Field of Search .................. 71/103, 98

[56] References Cited

U.S. PATENT DOCUMENTS

| | | | |
|---|---|---|---|
| 2,634,202 | 4/1953 | Fineke .................. | 71/103 |
| 3,138,519 | 6/1964 | Riden et al. .................. | 71/103 |
| 3,227,542 | 1/1966 | Kurtz et al. .................. | 71/103 |

FOREIGN PATENT DOCUMENTS 82,372 1/1975 Japan.
83,242 4/1975 Japan.
84,707 8/1975 Japan.

OTHER PUBLICATIONS

Gregory et al., Chem. Abst. vol. 58 (1963).

*Primary Examiner*—Catherine L. Mills
*Attorney, Agent, or Firm*—Oblon, Fisher, Spivak, McClelland & Maier

[57] ABSTRACT

A germicidal herbicide for agriculture and horticulture, which comprises at least one compound, as an active ingredient having the formula (I);

$$R-X-CH=CH-COOY \qquad (I)$$

wherein R represents an alkyl or alkenyl group having 1 to 20 carbon atoms, X represents S, SO or SO$_2$, and Y represents a hydrogen atom, an alkali metal, an alkaline earth metal, NH$_4$, an alkyl or alkenyl group having 1 to 20 carbon atoms, a polyalcohol residue which may have therein ether bonds formed by intramolecular or intermolecular dehydration, an acetal glycerol residue, or an oxyethylene (1 to 20 units) or oxypropylene group (1 to 20 units) terminated by an alkyl group having 1 to 20 carbon atoms.

7 Claims, No Drawings

GERMICIDAL HERBICIDE FOR AGRICULTURE AND HORTICULTURE

BACKGROUND OF INVENTION

1. Field of the Invention

This invention relates to a novel germicidal herbicide for agriculture and horticulture and, particularly relates to a germicidal herbicide for agriculture and horticulture comprising one or more compounds, as active ingredients, having formula (I);

$$R-X-CH=CH-COOY \qquad (I)$$

wherein R represents an alkyl or alkenyl group having 1 to 20 carbon atoms, X represents S, SO or $SO_2$, and Y represents a hydrogen atom, an alkali metal, an alkaline earth metal, $NH_4$, an alkyl or alkenyl group having 1 to 20 carbon atoms, a polyalcohol residue which may have therein ether bonds formed by intramolecular or intermolecular dehydration, an acetal glycerol residue, or an oxyethylene (1 to 20 units) or oxypropylene group (1 to 20 units) terminated by an alkyl group having 1 to 20 carbon atoms.

2. Description of the Prior Art

Recently, the field of agricultural chemicals has made considerable progress and as a result a number of new germicides and herbicides have been produced. However, some of these agricultural chemicals or either harmful to man and animals or, pollute the environment., and moreover their effects are unstable. These deficiencies, therefore, often pose social problems.

In view of the above circumstances, there continues to be a need for germicidal herbicides for agriculture and horticulture having stable effects and higher safety.

In order to provide germicidal herbicides for agriculture and horticulture meeting the above demands, the present inventors examined a number of compounds and as a result found that alkylsulfenyl acrylic acid, alkylsulfinyl acrylic acid and alkylsulfonyl acrylic acid derivatives represented by formula (I) exhibit excellent germicidal effects on a plant virus and exhibit herbicidal effects on various weeds. Based on this finding, the present invention has been accomplished.

SUMMARY OF THE INVENTION

Accordingly, an object of this invention is to provide a germicidal herbicide for agriculture and horticulture possessing both germicidal and herbicidal effects.

DETAILED DESCRIPTION OF THE PREFERRED EMBODIMENT

When the compounds of the present invention are used as germicides, they eliminate a wide variety of ill effects of plant diseases and are less phototoxic than other germicides. On the other hand, when they are used as herbicides, they show a long-lasting effects, exhibit a stable potency without changing their effects and potencies according to various conditions such as the soil to which they are applied, and present a negligible toxicity to human beings, animals and fish.

These compounds possess excellent spreadability, wetting ability and dispersability characteristics on plants because of their surface-active potency, and therefore, they may be used without any particular adjuvant.

"Suitable polyalcohols which may have therein ether bonds formed by intramolecular or intermolecular dehydration" and are within the scope of group Y of formula (I) include ethylene glycol, propylene glycol, glycerol, erythritol, xylitol, pentaerythritol, sorbitol, mannitol, and polyoxyalkylene glycols having diglycerine, dipentaerythritol, xylitan, sorbitan, mannitan and oxyethylene groups or oxypropylene groups having 2 to 20 units.

Suitable compounds within the scope of formula (I) include

---

1  β-alkylsulfenyl acrylic acids or salts
   n-$C_4H_9$—S—CH=CH—COONa, n-$C_8H_{17}$—S—CH=CH—COONa,
   n-$C_{12}H_{25}$—S—CH=CH—COONa, n-$C_{16}H_{33}$—S—CH=CH—COONa
   n-$C_4H_9$—S—CH=CH—COOH (mp86~88° C) n-$C_{12}H_{25}$—S—CH=CH—COOH (mp92~94° C)
   n-$C_8H_{17}$—S—CH=CH—COOH, n-$C_{10}H_{21}$—S—CH=CH—COOH, n-$C_{14}H_{29}$—S—CH=CH—COOH 2  β-alkylsulfinyl acrylic acids or salts
   n-$C_4H_9$—SO—CH=CH—COONa, n-$C_{10}H_{21}$—SO—CH=CH—COONa, n-$C_{12}H_{25}$—SO—CH=CH—COONa
   n-$C_4H_9$—SO—CH=CH—COOH (mp58~62° C) n-$C_{12}H_{25}$—SO—CH=CH—COOH (mp62~65° C)
   n-$C_8H_{17}$—SO—CH=CH—COOH 3  β-alkylsulfonyl acrylic acids or salts
   n-$C_4H_9$—$SO_2$—CH=CH—COOH (mp102~104° C) n-$C_{12}H_{25}$—$SO_2$—CH=CH—COOH (mp105~108° C)
   n-$C_{12}H_{25}$—$SO_2$—CH=CH—COONa 4  β-alkylsulfenyl acrylic acid alkyl esters
   n-$C_4H_9$—S—CH=CH—$COOCH_3$ (mp44~46° C) n-$C_{12}H_{25}$—S—CH=CH—$COOCH_3$ (mp48~50° C)
   n-$C_8H_{17}$—S—CH=CH—$COOCH_3$, n-$C_{18}H_{37}$—S—CH=CH—$COOCH_3$ 5  β-alkylsulfinyl acrylic acid alkyl esters
   n-$C_4H_9$—SO—CH=CH—$COOCH_3$ (mp53~55° C) n-$C_{12}H_{25}$—SO—CH=CH—$COOCH_3$ (mp55~58° C)
   n-$C_8H_{17}$—SO—CH=CH—$COOCH_3$, n-$C_2H_7$—SO—CH=CH—$COOCH_3$,
   n-$C_5H_{11}$—SO—CH=CH—$COOC_2H_5$, n-$C_{18}H_{37}$—SO—CH=CH—$COOCH_3$ 6  β-alkylsulfonyl acrylic acid alkyl esters
   n-$C_4H_9$—$SO_2$—CH=CH—$COOCH_3$ (mp83~85° C) n-$C_{12}H_{25}$—$SO_2$—CH=CH—$COOCH_3$ (mp85~88° C)
   n-$C_8H_{17}$—$SO_2$—CH=CH—$COOCH_3$, n-$C_{18}H_{37}$—$SO_2$—CH=CH—$COOCH_3$,
   n-$C_8H_{17}$—$SO_2$—CH=CH—$COOC_2H_5$ 7  β-alkylsulfenyl acrylic acid methylcarbityl esters
   n-$C_4H_9$—S—CH=CH—$COOCH_2CH_2OCH_2CH_2OCH_3$ ($n_D^{20}$ 1.5130)
   n-$C_{12}H_{25}$—S—CH=CH—$COOCH_2CH_2OCH_2CH_2OCH_3$ ($n_D^{20}$ 1.5210)

8  β-alkylsulfinyl acrylic acid methylcarbityl esters
   n-$C_4H_9$—SO—CH=CH—$COOCH_2CH_2OCH_2CH_2OCH_3$ ($n_D^{20}$ 1.5010)
   n-$C_{12}H_{25}$—SO—CH=CH—$COOCH_2CH_2OCH_2CH_2OCH_3$ ($n_D^{20}$ 1.5120)

9  β-alkylsulfonyl acrylic acid methylcarbityl esters
   n-$C_4H_9$—$SO_2$—CH=CH—$COOCH_2CH_2OCH_2CH_2OCH_3$ ($n_D^{20}$ 1.5115)
   n-$C_{12}H_{25}$—$SO_2$—CH=CH—$COOCH_2CH_2OCH_2CH_2OCH_3$ ($n_D^{20}$ 1.5210)

10 β-alkylsulfenyl acrylic acid glyceryl esters n-$C_4H_9$—S—CH=CH—$COOCH_2$—$\overset{\overset{OH}{|}}{CH}$—$CH_2OH$ ($n_D^{20}$ 1.5001)

n-$C_{12}H_{25}$—S—CH=CH—$COOCH_2$—$\overset{\overset{OH}{|}}{CH}$—$CH_2OH$ $$\text{n-C}_4\text{H}_9\text{—S—CH=CH—COOCH}_2\text{—}\overset{\overset{\displaystyle\text{OH}}{|}}{\text{CH}}\text{—CH}_2\text{OH} \quad (n_D^{20}\ 1.5001)$$

$$\text{n-C}_{12}\text{H}_{25}\text{—S—CH=CH—COOCH}_2\text{—}\overset{\overset{\displaystyle\text{OH}}{|}}{\text{CH}}\text{—CH}_2\text{OH} \quad (n_D^{20}\ 1.5098)$$

11 β-alkylsulfinyl acrylic acid glyceryl esters $$\text{n-C}_4\text{H}_9\text{—SO—CH=CHCOOCH}_2\text{—}\overset{\overset{\displaystyle\text{OH}}{|}}{\text{CH}}\text{—CH}_2\text{OH} \quad (n_D^{20}\ 1.5111)$$

$$\text{n-C}_{12}\text{H}_{25}\text{—SO—CH=CH—COOCH}_2\text{—}\overset{\overset{\displaystyle\text{OH}}{|}}{\text{CH}}\text{—CH}_2\text{OH} \quad (n_D^{20}\ 1.5120)$$

12 β-alkylsulfonyl acrylic acid glyceryl esters $$\text{n-C}_4\text{H}_9\text{—SO}_2\text{—CH=CH—COOCH}_2\text{—}\overset{\overset{\displaystyle\text{OH}}{|}}{\text{CH}}\text{—CH}_2\text{OH} \quad (n_D^{20}\ 1.5015)$$

$$\text{n-C}_{12}\text{H}_{25}\text{—SO}_2\text{—CH=CH—COOCH}_2\text{—}\overset{\overset{\displaystyle\text{OH}}{|}}{\text{CH}}\text{—CH}_2\text{OH} \quad (n_D^{20}\ 1.5092)$$

13 β-alkylsulfenyl acrylic acid glyceryl acetal esters n-C$_4$H$_9$—S—CH=CH—COOCH$_2$—[dioxolane with C(CH$_3$)$_2$] (mp 44~45° C)

n-C$_{12}$H$_{25}$—S—CH=CH—COOCH$_2$—[dioxolane with C(CH$_3$)$_2$] (mp 45~47° C)

14 β-alkylsulfinyl acrylic acid glyceryl acetal esters n-C$_4$H$_9$—SO—CH=CH—COOCH$_2$—[dioxolane with C(CH$_3$)$_2$] ($n_D^{20}$ 1.5678)

n-C$_{12}$H$_{25}$—SO—CH=CH—COOCH$_2$—[dioxolane with C(CH$_3$)$_2$] ($n_D^{20}$ 1.5068)

15 β-alkylsulfonyl acrylic acid glyceryl acetal esters n-C$_4$H$_9$—SO$_2$—CH=CH—COOCH$_2$—[dioxolane with C(CH$_3$)$_2$] ($n_D^{20}$ 1.5200)

n-C$_{12}$H$_{25}$—SO$_2$—CH=CH—COOCH$_2$—[dioxolane with C(CH$_3$)$_2$] ($n_D^{20}$ 1.5214)

16 β-alkylsulfenyl acrylic acid polyoxyalkylene esters
n-C$_4$H$_9$—S—CH=CH—COO(CH$_2$CH$_2$O)$_{15}$H ($n_D^{20}$ 1.5030)
n-C$_{12}$H$_{25}$—S—CH=CH—COO(CH$_2$CH$_2$O)$_{15}$H ($n_D^{20}$ 1.5230)
n-C$_4$H$_9$—S—CH=CH—COO(CH$_2$CH$_2$O)$_2$H 17 β-alkylsulfinyl acrylic acid polyoxyalkylene esters
n-C$_4$H$_9$—SO—CH=CH—COO(CH$_2$CH$_2$O)$_{15}$H ($n_D^{20}$ 1.5210)
n-C$_{12}$H$_{25}$—SO—CH=CH—COO(CH$_2$CH$_2$O)$_{15}$H ($n_D^{20}$ 1.5121)
n-C$_{14}$H$_{29}$—SO—CH=CH—COO(CH$_2$CH$_2$O)$_{15}$H
n-C$_{14}$H$_{29}$—SO—CH=CH—COO(CH$_2$CH$_2$CH$_2$O)$_5$H 18 β-alkylsulfonyl acrylic acid polyoxyalkylene esters
n-C$_4$H$_9$SO$_2$—CH=CH—COO(CH$_2$CH$_2$O)$_{15}$H ($n_D^{20}$ 1.5180)
n-C$_{12}$H$_{25}$—SO$_2$—CH=CH—COO(CH$_2$CH$_2$O)$_{15}$H ($n_D^{20}$ 1.5189)

19 β-alkylsulfenyl acrylic acid sorbityl esters n-C$_4$H$_9$—S—CH=CH—COO—CH$_2$—[pyranose ring with HO, OH, OH] (mp 40~41° C)

n-C$_{12}$H$_{25}$—S—CH=CH—COO—CH$_2$—[pyranose ring with HO, OH, OH] (mp 43~46° C)

20 β-alkylsulfinyl acrylic acid sorbityl esters n-C$_4$H$_9$—SO—CH=CH—COO—CH$_2$—[pyranose ring with HO, OH, OH] (mp 30~31° C)

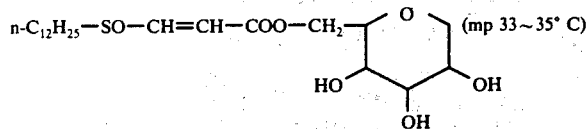

21 β-alkylsulfonyl acrylic acid sorbityl esters

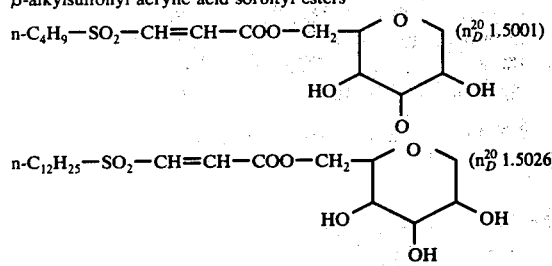

The compounds of formula (I) in the present invention can be produced, for example, as follows.

(a) Mercaptans of the formula;

RSH wherein R is defined as in formula (I) are reacted with proprolic acid derivatives in alkaline aqueous solution to obtain the compounds of formula (I) wherein X is S and Y is a hydrogen atom, alkali metal, alkaline earth metal or NH$_4$.

(b) Acids obtained in process (a), or acid halides thereof, are reacted with various alcohols in the presence of an acid or base catalyst in a conventional manner to obtain the compounds of formula (I) wherein X is S, and Y is an alkyl or alkenyl group having 1 to 20 carbon atoms, a polyalcohol residue which may have therein ether bonds formed by intramolecular or intermolecular dehydration, an acetal glycerol residue or, an oxyethylene (1 to 20 units) or oxypropylene (1 to 20 units) terminated by an alkyl group having 1 to 20 carbon atoms.

(c) The compounds thus obtained in processes (a) and (b) may be oxidized with an inorganic or organic peroxide such as sodium metaperiodate, hydrogen peroxide, perbenzoic acid, m-chloroperbenzoic acid and peracetic acid to obtain the corresponding compounds of formula (I) wherein X is SO or SO$_2$ according to the methods of (Japanese Patent Applications Nos. 82372/1975, 83242/1975 and 84707/1975.

The compounds of formula (I) may be used singly as germicides for agriculture and horticulture without any other adjuvants. They can also be used in the form of wettable powders or solutions or in other forms applicable to general agricultural chemicals, such as dissolving, suspending or emulsifying them in or mixing them with conventional carriers.

The compounds of formula (I) may be used as a germicide in a concentration ranging from 300 to 1,000 ppm, preferably 500 ppm.

The present compounds can exterminate plant diseases by spraying them on growing plants. Moreover, they can be used as an antiseptic by immersing seeds and bulbs therein.

The compounds of formula (I) according to the present invention possess a particularly strong herbicidal potency to gramineae weeds such as barnyardgrass, Cyperus microiria, Henry crabgrass, goosegrass and green foxtail; broad-leaved weeds such as Polygonum blumei, livid amaranth, common purslane and common lambsquarters; and perennial weeds such as purple nutsedge and Rumex japonicus. They can be used singly and also in the conventional forms of a powder, granules, wettable powder, emulsions and the like by dissolving, suspending or emulsifying them in carriers, or by mixing them with carriers. The compounds of formula (I) may usually be used as a herbicide in a concentration ranging from 3,000 to 6,000 ppm, preferably 4,000 ppm.

Suitable solid carriers include mineral powder such as clays, for example, kaolin, bentonite and terra abla; talcs, for example, talcum powder; silicates, for example, diatomaceous earth, vermiculite, slaked lime and mica powder; and alumina, silica gel and the like. Suitable liquid carriers include, for example, water, alcohols, ketones, benzene, xylene, toluene and cyclohexane.

Since compounds of the formula (I) possess surface-active potency by themselves, particular surface-active agents are not necessarily required. However, conventional surface-active agents, such as spreaders, emulsifiers, penetrants, dispersants and solublizers may be used as needed for example, soaps, higher alcohol sulfates, alkyl sulfonates, alkylaryl sulfonates, quaternary ammonium salts, polyalkylene oxides, higher fatty acid esters and the like.

Germidical herbicides for agriculture and horticulture according to the present invention may be used, if necessary, in combination with other herbicides, insecticides, fertilizer components, soil-improving agents or germicides.

The invention is illustrated below in further detail with reference to the following Examples.

EXAMPLE 1

A mixture of 25 parts by weight of n—C$_4$H$_9$SCH=CHCOOCH$_3$, 5 parts by weight of diisobutylene-disodium malate copolymer powder and 70 parts by weight of clay was fully crushed to obtain a wettable powder.

EXAMPLE 2

40 parts by weight of n—C$_4$H$_9$SOCH=CHCOOCH$_3$, 20 parts by weight of polyoxyethylene (20) sorbitan monooleate and 40 parts by weight of cyclohexane were mixed to obtain an emulsifiable concentrate.

EXAMPLE 3

In plastic pots of 15 cm length, 10 cm width and 8 cm height was placed field soil. Each of these was planted with 20 grains of seeds of the weeds shown in Table 1 and with 20 grains of seeds of the crops shown in Table 1.

On the 2nd and 7th days after these seeds were covered with soil, test compounds (15 ml/pot: corresponding to 500 g of active ingredient per 10a) were sprayed on the whole surface. On the 14th day after spraying, the inhibitory effect on weed growth and the harmful effect on the crops were investigated.

The results obtained are as also shown in Table 1.

50% of the active component. At the time of use, it was diluted 1,000-fold with water.

EXAMPLE 5 (Emulsifiable concentrate)

A mixture of 10 parts by weight of n—$C_{12}H_{25}SCH=CHCOOH$, 10 parts by weight of acetone, 20 parts by weight of emulsifier (higher fatty acid esters) and 60 parts by weight of water was dissolved to obtain an emulsifiable concentrate containing 10% of the active component. At the time of use, it was diluted 200-fold with water.

EXAMPLE 6 (Exterminating effect on rice blight leaf spot disease)

Table 1

| Test compounds | Inhibitory effect on weed-growth | | | | | | | Harmful effect on crops | | | |
|---|---|---|---|---|---|---|---|---|---|---|---|
| | henry crab-grass | green foxtail | livid ama-ranth | Poly-gonum Blumei | Common lambs-quarters | Common purs-lane | Rumex Japonicus | corn | red bean | soy-bean | pea-nut |
| n-$C_4H_9$SCH=CHCOOH | 5 | 5 | 5 | 5 | 5 | 5 | 4.5 | 0 | 0 | 0 | 0 |
| n-$C_4H_9$SCH=CHCOOCH$_3$ | 5 | 5 | 5 | 5 | 5 | 5 | 5 | 0 | 0 | 0 | 0 |
| n-$C_4H_9$SCH=CHCOOCH$_2$CHCH$_2$OH (OH) | 4 | 4 | 4.5 | 4.5 | 4.5 | 4.5 | 4 | 0 | 0 | 0 | 0 |
| n-$C_4H_9$SCH=CH—COO(CH$_2$CH$_2$O)$_2$H | 5 | 5 | 5 | 5 | 5 | 5 | 5 | 0 | 0 | 0 | 0 |
| n-$C_4H_9$SCH=CH—COOCH$_2$—(sugar ring) | 5 | 5 | 5 | 5 | 5 | 5 | 5 | 0 | 0 | 0 | 0 |
| n-$C_4H_9$SCH=CH—COOCH$_2$—(dioxolane) | 5 | 5 | 5 | 5 | 5 | 5 | 5 | 0 | 0 | 0 | 0 |
| n-$C_4H_9$SOCH=CHCOOH | 5 | 5 | 5 | 5 | 5 | 5 | 4.5 | 0 | 0 | 0 | 0 |
| n-$C_4H_9$SOCH=CHCOOCH$_3$ | 5 | 5 | 5 | 5 | 5 | 5 | 5 | 0 | 0 | 0 | 0 |
| n-$C_4H_9$SOCH=CH—COO(CH$_2$CH$_2$O)$_{15}$H | 4 | 4 | 4 | 4 | 4 | 4 | 4 | 0 | 0 | 0 | 0 |
| n-$C_4H_9$SOCH=CH—COONa | 5 | 5 | 5 | 5 | 5 | 5 | 5 | 0 | 0 | 0 | 0 |
| n-$C_4H_9$SO$_2$CH=CHCOOH | 5 | 5 | 5 | 5 | 5 | 5 | 4.5 | 0 | 0 | 0 | 0 |
| n-$C_4H_9$SO$_2$CH=CHCOOCH$_3$ | 5 | 5 | 5 | 5 | 5 | 5 | 5 | 0 | 0 | 0 | 0 |
| n-$C_8H_{17}$SCH=CHCOOH | 4 | 4 | 4 | 4.5 | 4 | 4 | 3.5 | 0 | 0 | 0 | 0 |
| n-$C_8H_{17}$SCH=CHCOOCH$_3$ | 4 | 4.5 | 4 | 4.5 | 4 | 4 | 4 | 0 | 0 | 0 | 0 |
| n-$C_8H_{17}$SOCH=CHCOOH | 5 | 5 | 4 | 4 | 4 | 4 | 4 | 0 | 0 | 0 | 0 |
| n-$C_8H_{17}$SOCH=CHCOOCH$_3$ | 5 | 5 | 4 | 4 | 4 | 4 | 4 | 0 | 0 | 0 | 0 |
| n-$C_8H_{17}$SO$_2$CH=CHCOOCH$_3$ | 3 | 3 | 3 | 3 | 3 | 2 | 2 | 0 | 0 | 0 | 0 |
| n-$C_{12}H_{25}$SCH=CHCOONa | 3 | 3 | 3 | 3 | 3 | 3 | 3 | 0 | 0 | 0 | 0 |
| n-$C_{12}H_{25}$SCH=CHCOOCH$_3$ | 3 | 3 | 3 | 3 | 3 | 3 | 3 | 0 | 0 | 0 | 0 |
| n-$C_{12}H_{25}$SOCH=CHCOOCH$_3$ | 4 | 4 | 3 | 3 | 3 | 3 | 2 | 0 | 0 | 0 | 0 |
| n-$C_{12}H_{25}$SO$_2$CH=CHCOOH | 4 | 4 | 2 | 3 | 3 | 3 | 3 | 0 | 0 | 0 | 0 |
| n-$C_{12}H_{25}$SO$_2$CH=CHCOOCH$_3$ | 3 | 3 | 2 | 2 | 2 | 2 | 2 | 0 | 0 | 0 | 0 |
| n-$C_{13}H_{37}$SCH=CHCOOCH$_3$ | 3 | 3 | 2 | 2 | 2 | 2 | 2 | 0 | 0 | 0 | 0 |
| n-$C_{13}H_{37}$SOCH=CHCOOCH$_3$ | 2 | 2 | 2 | 2 | 2 | 2 | 1 | 0 | 0 | 0 | 0 |
| n-$C_{13}H_{37}$SO$_2$CH=CHCOOCH$_3$ | 2 | 2 | 2 | 2 | 2 | 2 | 1 | 0 | 0 | 0 | 0 |
| Trifururaline emulsifiable concentrate | 5 | 5 | 5 | 4.5 | 5 | 5 | 2 | 3 | 4 | 2 | 1 |

Note:
Inhibitory effect on weed-growth
5 total inhibition
4 80% inhibition
3 60 % inhibition
2 40% inhibition
1 20% inhibition
0 no effect
Harmful effect on crops
4 withering
3 severe harm
2 moderate harm
1 slight harm
0 no effect

EXAMPLE 4 (Wettable powder)

A mixture of 50 parts by weight of n—$C_{12}H_{25}SCH=CHCOONa$, 5 parts by weight of surface-active agent (alkylbenzenesulfonates and higher alcohol sulfates) and 45 parts by weight of clay was fully crushed to obtain a wettable powder containing In each plastic pot of 16 cm length, 10 cm width and 5 cm height were bred 20 stubbles of rice plants (Species, Japanese line weather) in a hothouse. At the 4th leaf stage, 20 ml of a solution or hydrate containing 500 ppm of the test compounds per pot were sprayed over the plant bodies. After spraying, the plants were allowed to stand in a hothouse, and then spores of rice blight fungi, cultured in a test tube, were suspended in water, and then inoculated on the plant bodies by a homogeneous spray. Then the plants were placed at a constant temperature 27° C. and more than 95% relative humidity. On the 5th day after infection, the number of infected spots per leaf was counted. The control value was calculated from a comparison with untreated plants. The results obtained are shown in Table 2.

the surface of leaves were investigated, and the control value was calculated. The results obtained are shown in Table 3.

Table 3

| Test compounds | Concentration of active ingredients (ppm) | Control value (%) | Phyto-toxicity |
|---|---|---|---|
| $n$-$C_8H_{17}SOCH=CHCOOCH_3$ | 500 | 60 | — |
| $n$-$C_8H_{17}SO_2CH=CHCOOC_2H_5$ | 500 | 72 | — |
| $n$-$C_{10}H_{21}SCH=CHCOOH$ | 500 | 100 | — |
| $n$-$C_{10}H_{21}SOCH=CHCOONa$ | 500 | 81 | — |
| $n$-$C_{12}H_{25}SCH=CHCOONa$ | 500 | 100 | — |
| $n$-$C_{12}H_{25}SCH=CHCOOCH_3$ | 500 | 87 | — |
| $n$-$C_{12}H_{25}SOCH=CHCOONa$ | 500 | 60 | — |
| $n$-$C_{12}H_{25}SOCH=CHCOOCH_2$—[dioxane ring with CH_3, CH_3] | 500 | 89 | — |
| $n$-$C_{14}H_{29}SCH=CHCOOH$ | 500 | 98 | — |
| $n$-$C_{14}H_{29}SOCH=CHCOO(CH_2 . CH_2 . CH_2O)_5H$ | 500 | 91 | — |
| $n$-$C_{16}H_{33}SCH=CHCOONa$ | 500 | 72 | — |
| Commercial germicide* (1,500-fold dilution) | | 90 | — |
| Control | | | — |

*It contains 70 parts by weight of 1,2-bis(3-methoxycarbonyl-2-thioureide as an active ingredient.
— : no harm EXAMPLE 8 (Exterminating effect on vegetable black rot (soft rot)

Slices (length 3 cm, width 2 cm) of white stems of

Table 2

| Test compounds | Concentration of active ingredients (ppm) | Control value (%) | Phyto-toxicity |
|---|---|---|---|
| $n$-$C_8H_{17}SCH=CHCOONa$ | 500 | 65 | — |
| $n$-$C_{10}H_{21}SCH=CHCOOH$ | 500 | 71 | — |
| $n$-$C_{10}H_{21}SOCH=CHCOONa$ | 500 | 50 | — |
| $n$-$C_{12}H_{25}SCH=CHCOONa$ | 500 | 100 | — |
| $n$-$C_{12}H_{25}SCH=CHCOOCH_3$ | 500 | 97 | — |
| $n$-$C_{12}H_{25}SOCH=CHCOONa$ | 500 | 60 | — |
| $n$-$C_{12}H_{25}SCH=CHCOOCH_2$—[dioxane ring with CH_3, CH_3] | 500 | 82 | — |
| $n$-$C_{12}H_{25}SCH=CHCOOCH_2$—[tetrahydropyran ring with HO, OH, OH] | 500 | 91 | — |
| $n$-$C_{12}H_{25}SO_2CH=CHCOONa$ | 500 | 89 | — |
| $n$-$C_{12}H_{25}SCH=CHCOOCH_2CH_2OCH_2CH_2OCH_3$ | 500 | 78 | — |
| $n$-$C_{12}H_{25}SCH=CHCOOCH_2$—CH(CH)—$CH_2OH$ | 500 | 58 | — |
| $n$-$C_{12}H_{25}SOCH=CHCOOCH_2$—CH(OH)—$CH_2OH$ | 500 | 72 | — |
| $n$-$C_{14}H_{29}SCH=CHCOOH$ | 500 | 98 | — |
| $n$-$C_{14}H_{29}SOCH=CHCOO(CH_2CH_2O)_{15}H$ | 500 | 62 | ± |
| Commercial germicide* (1,500-fold dilution) | | 71 | ± |
| Control | | 0 | — |

* It contains 30 parts by weight of o-ethyl-S,S-diphenyl-dithiophosphate
— : no harm
± : slight harm EXAMPLE 7 (Exterminating effect on melones anthranose)

Cucumber plants (Var., Su-yo) were placed in a series of pots. Twenty ml. of test compound, as a solution or hydrate of given concentration was sprayed over each pot. The next day, the plants were inoculated with a spore suspension of antranose fungi in an inoculation box at 27° C and more than 95% humidity with a microsprayer. Two days after, the plants were transferred to a green house, and 7 days late the infected spots on commercial chinese cabbages were made and immersed in solutions or wettable powder suspensions of a test compounds diluted to a given concentration. Then, they were air-dried, and inoculated with a suspension of spores of vegetable black rot fungi using a cluster of five needles. The slices were allowed to stand in an inoculation box at 27° C. and more than 95% humidity for one day. Infected spots were measured and the control value was calculated. The results obtained are shown in Table 4.

Table 4

| Test compounds | Concentration of active ingredients (ppm) | Control (%) valve | Phytotoxicity |
|---|---|---|---|
| n-C$_3$H$_7$SOCH=CHCOOCH$_3$ | 500 | 83 | — |
| n-C$_4$H$_9$SCH=CHCOONa | 500 | 91 | — |
| iso-C$_4$H$_9$SCH=CHCOOC$_2$H$_5$ | 500 | 63 | — |
| sec-C$_4$H$_9$SOCH=CHCOOCH$_3$ | 500 | 68 | — |
| n-C$_5$H$_{11}$SOCH=CHCOOC$_2$H$_5$ | 500 | 70 | — |
| Commercial germicide* (1,000-fold dilution) | | 53 | — |
| Control | | 0 | — |

*It contains 12.5 parts by weight of dihydrostreptomycin sulfate.
— : no harm

What is claimed as new and intended to be secured by Letters Patent is:

1. A method of inhibiting the growth of noxious weeds which comprises applying a herbicidally effective amount of at least one compound of the formula:

R—X—CH=CH—COOY wherein R represents an alkyl or alkenyl group having 1 to 20 carbon atoms, X represents S, SO or SO$_2$, and Y represents a hydrogen atom, an alkali metal, an alkaline earth metal, NH$_4$, an alkenyl group having 1 to 20 carbon atoms, a polyalcohol residue which may have therein ether bonds formed by intramolecular or intermolecular dehydration, an acetal glycerol residue, or an oxyethylene (1 to 20 units) or oxypropylene group (1 to 20 units) terminated by an alkyl group having 1 to 20 carbon atoms.

2. The method of claim 1 wherein X in formula (I) represents S.

3. The method of claim 1 wherein X in formula (I) represents SO.

4. The method of claim 1 wherein X in formula (I) represents SO$_2$.

5. The method of claim 1 wherein said active ingredient is n—C$_4$H$_9$SCH=CHCOOCH$_3$ or
n—C$_4$H$_9$SOCH=CHCOOCH$_3$.

6. The method of claim 1 wherein said active ingredient is n—C$_{12}$H$_{25}$SCH=CHCOONa or
n—C$_{12}$H$_{25}$SCH=CHCOOH.

7. The method of claim 1, wherein said herbicidally effective amount is a concentration of from 3,000 to 6,000 ppm.

* * * * *